United States Patent [19]

Theoharides

[11] Patent Number: 5,648,355
[45] Date of Patent: *Jul. 15, 1997

[54] METHOD OF TREATMENT OF ENDOGENOUS, PAINFUL GASTROINTESTINAL CONDITIONS OF NON-INFLAMMATORY, NON-ULCERATIVE ORIGIN

[75] Inventor: Theoharis C. Theoharides, Brookline, Mass.

[73] Assignee: KOS Pharmaceutical, Inc., Miami, Fla.

[*] Notice: The term of this patent shall not extend beyond the expiration date of Pat. No. 5,250,529.

[21] Appl. No.: 193,597

[22] Filed: Feb. 9, 1994

[51] Int. Cl.$^6$ .......... A61K 31/495; A61K 31/42; A61K 31/35; A61K 31/21
[52] U.S. Cl. .......... 514/255; 514/381; 514/457; 514/510; 514/579; 514/650; 514/673
[58] Field of Search .......... 514/255, 381, 514/457, 510, 579, 650, 673

[56] References Cited

U.S. PATENT DOCUMENTS

| | | | |
|---|---|---|---|
| 4,507,321 | 3/1985 | Raisfeld | 514/673 |
| 4,843,074 | 6/1989 | Rzeszotarski et al. | 514/228.2 |
| 5,057,322 | 10/1991 | Frost | 424/474 |
| 5,250,529 | 10/1993 | Theoharides | 514/255 |

FOREIGN PATENT DOCUMENTS

WO93/12773   8/1993   WIPO.

OTHER PUBLICATIONS

Pothoulakis et al., "CP-96,345, a substance P antagonist, inhibits rat intestinal responses to *Clostridium difficile* toxin A but no cholera toxin", Proc. Natl. Acad. Sci., vol. 91, pp. 947–951, Feb. 1994.

Pothoulakis et al., "Ketotifen Inhibits *Clostridium difficile* Toxin A–Induced Enteritis in Rat Ileum", Gastroenterology 1993, vol. 105, pp. 701–707.

Castagliuolo et al., "Neuronal Involvement In The Intestinal Effects Of *Clostridium difficile* Toxin A And Vibrio Cholera Enterotoxin In Rat Ileum", Gastroenterology, 104:A677, 104:A679, 1993.

Weston, et al. "Terminal Ileal Mucosal Mast Cells in Irritable Bowel Syndrome", *Digestive Diseases and Sciences*, 38(9):1590–1595, 1993.

Read, "Irritable Bowel Syndrome (IBS)—Definition and Pathophysiology", *Scand. Jrn. Gastroenterol.*, 130:7–13, 1987.

Stefanini, et al. "Oral Disodium Cromoglycate Treatment on Irritable Bowel Syndrome: An Open Study on 101 Subjects with Diarrheic Type", *Am. Jrnl. of Gastroenterology*, 87(1):55–57, 1992.

Martin, et al. "Comparison of the Inhibitory Effects of Spermine, Papaverine and Adrenaline Upon Isolated Segments . . . ", *Clin. & Exper. Pharma. & Physiology*, 13:87–90, 1986.

Cartagena, et al. "Inhibition of Mast Cell Degranulation by Natural Polyamines", *Federation Proceedings*, 45:1648, 1986.

Page, et al. "Treatment of the Irritable Syndrome with Bentyl® (Dicyclomine Hydrochloride)", *Clin. Gastroenterol.*, 3:153–156, 1981.

Aihara, et al. "Polyamine Inhibition of Gastric Ulceration and Secretion in Rats", *Biochemical Pharmacology*, 32(11):1733–1736, 1983.

McCormack, et al. "Polyamines are necessary for cell migration by a small intestinal crypt cell line", *Am. Jrnl. of Physiology*, 264(2):G367–G374, 1993.

Auricchio, et al. "Amines Protect In Vitro the Celiac Small Intestine From the Damaging Activity of Gliadin Peptides", *Gastroenterology*, 99:1668–1674, 1990.

Stern, et al. "Contribution to pharmacology of spermidine", *Glas Srpske Akademije Nauka*, 24:43–50, 1971 (See abstract).

Chemical Abstracts; Ferzoco et al., "Counterregulation of a Prokinetic Calcium–Dependent Mechanism by CAMP–Dependent Agents in Isolated Segments of Terminal Ileum"; Abstract No. 119: 41390 (See Abstract).

*Primary Examiner*—Kevin E. Weddington

[57] ABSTRACT

A method for treating endogenous, painful gastrointestinal conditions of non-inflammatory, non-ulcerative origin, such as abdominal migraine and irritable bowel syndrome, entails administering a pharmacologically effective amount of a mast cell degranulation-blocking agent.

21 Claims, No Drawings

METHOD OF TREATMENT OF ENDOGENOUS, PAINFUL GASTROINTESTINAL CONDITIONS OF NON-INFLAMMATORY, NON-ULCERATIVE ORIGIN

BACKGROUND OF THE INVENTION

The present invention relates to treating endogenous, painful gastrointestinal conditions, such as abdominal migraine and irritable bowel syndrome, which involve neither inflammation nor ulcers. "Endogenous" in this context denotes a condition that is not attributed to an exogenous casual factor such as a food allergy, a bacterial or viral infection, a parasitic infestation, a drug reaction or trauma. More specifically, the present invention relates to treating a patient suffering from such a condition with a pharmaceutically effective amount of a mast cell degranulation-blocking agent.

The phrase "abdominal pain" indicates pain associated with the gastrointestinal tract. Functional abdominal pain usually is classified either as dyspepsia not associated with ulcers or as irritable bowel syndrome.

Irritable bowel syndrome (IBS), also known as "spastic colon" and "mucous colitis," is an intestinal motility disorder and ranks among the most common pathological conditions of the intestine. IBS is characterized by periodic or chronic bowel symptoms which include abdominal pain, diarrhea, constipation, a sense of incomplete evacuation, bloating, and excess gas sensation. This disorder seems to afflict type A (highly driven, perfectionist) personalities predominantly, and is two to five times more prevalent in women (20 times higher in Jewish women) than in men. It affects about 3 percent of the population. Drossman, *Hospital Practice* 93:95–108 (1988).

Pain and flatulence are the most prominent symptoms in patients suffering from IBS. The pain is usually situated in the left lower quadrant or suprapubically. It may be worse just before defecation and may lessen slowly afterward. Certain foods may precipitate the symptoms. When diarrhea is the main complaint, the stool often is watery but not bloody. The diarrhea frequently is worst in the morning and improves during the day. Some patients complain of pain in the left upper quadrant that is often brought on by meals and is very consistent in nature. In these patients, plain abdominal X-rays demonstrate air in the splenic flexure. Although this variant of IBS has been called "splenic flexure syndrome," there is no evidence that its pathogenesis differs from that of other manifestations of the disorder.

Many patients relate an exacerbation of symptoms to episodes of emotional stress. Fear of underlying cancer is common. In children of school age, IBS presents primarily with pain. Pain is usually periumbilical or in the left lower quadrant and is cramping in nature.

Many patients also experience abdominal pain that is endogenous but that is associated with nausea, bowel peristalsis and flatulence without diarrhea or constipation, the symptoms commonly seen with IBS. Such abdominal pain also can be associated with classic symptoms of migraine, such as one-sided headache with possible involvement of one eye and visual disturbances in that eye. Axon et al., *J. Clin. Gastroenterol.* 13: 615–16 (1991). By the same token, about 30–50% of patients diagnosed with IBS have frequent headaches, as compared to less than 15% in the control population. Watson et al., *Can. Med. Assoc. J.* 118: 387–98 (1978); Whorwell et al., *Gut* 27: 37–40 (1986). Finally, abdominal pain and associated symptoms can occur in the absence of a headache and still be considered a "migraine equivalent," especially in children. Lundbert, *Headache* 15: 122–25 (1975).

It is appropriate, therefore, to consider the pathophysiology and therapy of the category of endogenous, painful gastrointestinal conditions of non-inflammatory, non-ulcerative origin, including but not limited to abdominal migraine and IBS.

There is no effective therapy for IBS or related, endogenous gastrointestinal conditions. Thus, while various compounds have been described as useful in treating IBS, including 9H-fluorenyl-substituted amino acid derivatives (U.S. Pat. No. 5,079,260), benzodiazepine derivatives (U.S. Pat. No. 4,970,207), certain substituted sulfonamides (European application No. 0 404 440), and mu opiate receptor antagonists or "blockers" (U.S. Pat. No. 4,684,620), none of the disclosed treatment approaches in fact have proven successful. See, for example, *J. Gastroenterol.* 95: 232–41 (1988).

Similarly, no effective remedy exists for abdominal migraine. Development of a treatment has been hindered in part by the fact that the condition often presents without headache and any of the prodromal symptoms (nausea, vomiting, photophobia, sonophobia) typically associated with ordinary migraine.

For example, agents that prevent vasodilation, such as the β-blocker propranolol, seem not to work, since the abdominal pain appears not to be associated with the vasculature, in contrast to the migraine headache. By the same token, none of the drugs used prophylactically or acutely (symptomatically) for the treatment of migraine headaches would be expected to work, since the prophylactic agents prevent vasodilation while the acute agents constrict dilated vessels. Moreover, drugs effective against migraine headaches must cross the blood-brain barrier, while a drug effective against abdominal migraine would be concentrated preferentially in the intestine. Also, intracranial mast cells which have been associated with migraine headaches, see Theoharides, *Life Sciences* 46: 607–17 (1980), and U.S. Pat. No. 5,250,529, differ from gastrointestinal mast cells. For instance, the former but not the latter are inhibited by disodium cromoglycate. Pierce et al., *J. Immunol.* 128: 2481–86 (1982); Labracht-Hall et al., *Neuroscience* 39:199–207 (1990).

SUMMARY OF THE INVENTION

It is an object of the present invention, therefore, to provide an effective treatment for the above-described category of endogenous gastrointestinal conditions which avoids the lack of success and other problems associated with past efforts to this end.

In accomplishing this objective and others, there has been provided, in accordance with one aspect of the present invention, a method for treating endogenous, painful gastrointestinal conditions of non-inflammatory, non-ulcerative origin, which method comprises administering to a patient a pharmacologically effective amount of a mast cell-degranulation blocking agent.

In a preferred embodiment, the mast cell-degranulation blocking agent is selected from the group consisting of naturally occurring polyamines, heterocyclic histamine-1 receptor antagonists, histamine-3 receptor agonists, and agents that counteract the influence of female sex hormones (female sex hormone antagonists or inhibitors, referred to collectively as "anti-female sex hormones"). In other preferred embodiments the mast cell-degranulation blocking agent is spermine or spermidine, hydroxyzine or ketotifen, α,β-difluoro-N$^α$-fluoromethyl histamine, tamoxifen or a gonadotropin-releasing hormone (luteinizing hormone releasing hormone) analogue. In yet other preferred embodiments, the mast cell-degranulation blocking agent is N$^α$-dimethyl histamine, R$^α$-methyl histamine, α,β-dimethyl-N$^α$(dimethyl) histamine, α,β-difluoro-N$^α$(dimethyl) histamine, α-methyl,β-fluoro-N$^α$(fluoromethyl) histamine, clomiphene, mifepristone, tamoxifen, and a GnRH analogue such a LUPRON (leuprolide acetate).

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Mast cells are normal components of the connective and mucosal tissues and play an important role in allergy. These cells are mostly localized in the gastrointestinal mucosa, skin and lung. Mast cells are so located, it is believed, because these tissues are the main entry points for infective organisms and allergens, the chemicals that trigger the body's immune response. Recent evidence indicates that mast cells in the mucosa of the small intestine differ from mast cells in other tissues, especially connective tissues as well as brain. These mucosal mast cells also have been shown to be in close proximity to nerve endings. See Stead et al., *J. Gastroenterol.* 97:575–85 (1989).

Every mast cell contains up to 500 secretory granules, each storing more than 20 potent biological compounds. Mast cells secrete the contents of these granules, i.e., degranulate, when triggered by various specific and non-specific mechanisms. Accordingly, "degranulation" is used in this description to denote the release of any or all mediators from any or all mast cell secretory granules, whether in parallel, differentially or selectively.

The degranulation of mast cells in response to various agents is usually a biological consequence of the activation of one or more receptors located on the surface of the mast cell. The best known of these are the immunoglobulin E (IgE) receptors involved in allergic reactions, to date the most fully characterized pathological processes that involve mast cells. In this context IgE binds strongly to mast cells through its Fc receptor. When mast cell-bound IgE reacts with an antigen, the latter bridges two or more IgE molecules and causes mast cell degranulation with subsequent release of mediators, either stored or synthesized during mast cell degranulation.

There also is evidence that neurotransmitters such as acetylcholine and neuropeptides such as substance P, all being molecules that are released from neurons in the central (brain) and peripheral (gastrointestinal) nervous systems, may augment or trigger mast cell degranulation primarily through specific receptors, for example, in response to stress. In particular, research has shown that direct nerve stimulation causes mast cell activation and release of relevant chemical agents. See, for instance, Dimitriadou et al., *Neuroscience* 44: 97–112 (1991); Theoharides, *Life Sciences* 46: 607–17 (1990). Female sex hormones such as estradiol and progesterone likewise may augment or trigger mast cell degranulation. See Vliagoftis et al., *Int'l Arch. Allergy Immunol.* 98: 398–409 (1992); 93: 113–19 (1990). Thus, it has been shown that rat basophilic leukemia (RBL) cells, which mimic mucosal mast cells, bind progesterone. Kouretas et al., *Clinical Res.* 39:320 (1991).

Other triggers of mast cell degranulation include viral and bacterial toxins, drugs such as aspirin, morphine and curare, contrast media used in radiology, extreme heat, cold, solar radiation and hyperosmotic media. It is deemed important, therefore, to block the mast cell degranulation which all of these stimuli elicit, rather than to antagonize specific receptors, such as opioid receptors as taught in U.S. Pat. No. 4,684,620.

The compounds released by the mast cells following degranulation are known to cause many biological processes which are part of the overall response of the body to invasion by infective organisms and allergens. Examples of such processes are vasoconstriction or vasodilation, leukocyte chemotaxis, and pain.

Compounds released by mast cell degranulation which may be associated with irritable bowel syndrome include bradykinin, histamine, leukotrienes, prostaglandins, serotonin, tumor necrosis factor and vasoactive intestinal peptide. Interleukins and proteolytic enzymes, which can affect intestinal function, can augment pain or cause pain directly.

Histamine and other mediators bind to specific receptors on the surface of endothelial cells on vessels or on peripheral sensory neurons which become activated, directly or indirectly (through vessel tone), to transmit pain stimuli. Vasodilation and chemoattraction permit lymphocytes to leave the circulation and enter the tissue, where they cause additional mast cell degranulation and other responses. The process of degranulation continues, eventually involving many mast cells.

Mast cell degranulation, especially in response to neurohormonal triggers, now has been discovered to contribute to the symptoms experienced by patients suffering from abdominal migraine, irritable bowel syndrome and other endogenous, painful gastrointestinal conditions of non-inflammatory, non-ulcerative origin. It also has been found that an effective treatment for such conditions entails the administration of a mast cell degranulation-blocking agent, i.e., a compound that counteracts mast cell degranulation-inducing stimuli, either by binding to specific receptors or by inactivating crucial steps in the degranulation process.

The aforementioned correlation between mucosal mast cells and stimuli associated with IBS and related, endogenous conditions has not been documented heretofore. For instance, histologic sections of colonic tissue biopsied from a patient with irritable bowel syndrome were stained with monoclonal anti-tryptase antibody to identify tryptase-immunoreactive mast cells, and other sections were stained with polyclonal anti-SP antibody to reveal nerve fibers positive for substance P, a nociceptive neuropeptide capable of degranulating mast cells. Microscopic examination of the sections revealed numerous mast cells, identifiable by staining for tryptase, a proteolytic enzyme which is specific for the mast cells, and numerous nerve fibers stained for their content of substance P. Particularly noteworthy in this context was the close anatomic association observed to exist between mucosal mast cells and substance P-containing nerve fibers.

For the purposes of this description, the range of "mast cell degranulation-inducing stimuli" is illustrated by: (i)

immune molecules, for example, immunoglobulin (IgE), anaphylatoxins such as C5a, and cytokines such as tumor necrosis factor; (ii) neural substances, including neurotransmitters such as acetylcholine and neuropeptides such as substance P, calcitonin gene related peptide and vasoactive intestinal peptide; (iii) hormones, such as estrogens and progestins; and (iv) any other molecules that may be liberated within the body during endogenous conditions such as stress. Particularly preferred mast cell degranulation-blocking agents are: (a) natural polyamines; (b) certain heterocyclic histamine-1 receptor antagonists; (c) histamine-3 receptor agonists and (d) anti-female sex hormones.

Among the preferred polyamines are spermine and spermidine, as well as metabolites, including acetylated metabolites thereof and oxidized metabolites, of these two compounds. See Vliagoftis et al., *Biochem. Pharmacol.* 43:2237–45 (1992), the contents of which are hereby incorporated by reference.

Exemplary of the heterocyclic histamine-1 (H-1) receptor antagonists which are particularly suitable for the present invention, by virtue of their potency in inhibiting neuronally-induced mast cell secretion (as distinct from immunologic degranulation of mast cells), are Azelastine, Azatadine, Cetirizine, Hydroxyzine, Ketotifen, Loratadine and Oxatomide. A particularly suitable agent of this type is Ketotifen (Sigma Chemicals; St. Louis, Mo.) and the pharmaceutically acceptable, non-toxic salts thereof.

Pursuant to the present invention, suitable H-1 receptor antagonists are those that display an affinity for the H-1 receptor that is greater than about $5 \times 10^{-5}$ M. It is important in this regard to distinguish such high-affinity H-1 receptor antagonists from others of lower affinity which actually cause mast cell degranulation and, hence, should be avoided. See Pini et al., *Agents & Actions* 8:491–96 (1978). Examples of the latter type of compound appear in Table 1.

TABLE 1

HISTAMINE-1 RECEPTOR ANTAGONISTS
THAT CAUSE MAST CELL DEGRANULATION

| Compound | $ED_{20}$ for Histamine Release |
| --- | --- |
| Clorphenyramine | $10^{-3}$ M |
| Cyclizine | $5 \times 10^{-4}$ M |
| Diphenhydramine | $10^{-3}$ M |
| Promethazine | $10^{-4}$ M |

$ED_{20}$ = effective dose causing 20% secretion.
M = molar concentration.

Illustrative histamine-3 receptor agonists include $N^{\alpha}$-methyl histamine (Calbiochem Corporation, LaJolla, Calif.), $N^{\alpha}$-methyl-α(dimethyl) histamine and α,β-difluoro-$N^{\alpha}$(fluoromethyl) histamine.

Particularly preferred among the anti-female sex hormones are tamoxifen or (NOLVADEX Zeneca Pharmaceuticals; Wilmington, Del.), clomiphene or SEROPHENE Serono Labs; Norwell, Mass.), and analogues of gonadotropin releasing hormone (GnRH), a/k/a "luteinizing hormone releasing hormone" (LHRH), such as leuprolide acetate (LUPRON TAP Pharmaceuticals, Deerfield, Ill.).

Some of the classes of drugs which fall into the above-discussed category of mast cell degranulation-blocking agents are listed below, along with specific examples under each class:

Anthranilic Acid Derivatives
    N-(3,4-dimethoxycinnamoyl) anthranilic acids
Anti-Female Sex Hormones
    Clomiphene
    Mifepristone
    Tamoxifen
    GnRH analogues
Arachidonic Acid Metabolites
    Leukotriene $D_4$
    Lipoxin B
    Prostaglandin $E_1$
    Prostaglandin $E_2$
Histamine-3 Receptor Agonists
    $N^{\alpha}$-methyl histamine
    $N^{\alpha}$-dimethyl histamine
    Rα-methyl histamine
    α,β-dimethyl-$N^{\alpha}$(dimethyl) histamine
    α,β-difluoro-$N^{\alpha}$(dimethyl) histamine
    α-methyl,β-fluoro-$N^{\alpha}$(fluoromethyl) histamine
    α,β-difluoro-$N^{\alpha}$(fluoromethyl) histamine
Histamine-1 Receptor Antagonists Characterized by a
    Three-Ring Structure
    Piperidine derivatives
    Azelastine
    Azatadine
    Burfroline
    Doxantrozole
    Forskolin
    Ketotifen
    Lodoxamide tromethamine
    Loperamide
    Loratadine
    Myricetin
    Oxatomide
    Pizotifen
    Proxicromil
    Piperazine derivatives
    1-(5-isoquinolinylsulfonyl)-2-methylpiperazine
    1-(1-hydroxy-5-isoquinolinylsulfonyl)piperazine
    1-[2-hydroxy-3-[(4-hydroxy-3 nitrocoumarin-7-yl) oxyl] propyl]-4-(4-chlorobenzyl) piperazine
    Cetirizine
    6-[3-[4-(4-chlorobenzyl)-1-piperazinyl]propoxy][1] benzo-pyranc [2,3-d]-1,2,3-triazol-9(1H)-one
    Etodroxizine
    Hydroxyzine
    N-(optionally substituted benzhydryl)-N'-(optionally substituted)piperazines
    9-chloro-5-oxo-7-(1H-tetrazol-5yl)-5H-[1]-benzopyrano [2,3-b]pyridine sodium salt pentahydrate
Peptides
    L-Asp-Ser-Asp-Pro-Arg
    Cyclosporin A
    Forssman antibody
    Interleukin-1 receptor antagonist
    Lymphocyte Inhibitory Factor (LIF)
    Substance P-receptor antagonist
    Somatostatin
Phosphatase Inhibitors
    Okadaic acid
    Calyculin
    Quercetin
    Kaemferol
    Nedocromil
    Minocromil
    Cromolyn Polyamines
  Putrescine
  Spermidine
  Spermine
Protein Kinase Inhibitors
  3-10-Dihydroxy-10[(dimethylamino) methyl]-2,3,9,10,11,12-hexahydro-9-methyl-9,12,-epoxy-1H-diindolo[1,2,3-fg-3',2',1'-Kd] pyrrolo [3,4-c] [2,6] benzodiazocin-1-one (UCH-01)
  Staurosporin
Proteoglycans
  Heparin
  Herudin
Quinoline Derivatives
  1,3-Oxazolo[4,5-h]quinolines
  2-Carboxypyrimidoquinolines
  3-Aminoquinolines
Thiophene Derivatives
  1-Methyl-2(1,3,4-oxadiazol-2(3H)-one-5-yl) Benzimidazole
Miscellaneous Compounds
  2-Substituted 3-dimethylamino-5,6-methylenedioxydines
  2-o-Propoxyphenyl-8-azapurin-6-one
  2-Ethoxyethyl-5-chloro-benzoxazole-2-carboxylate
  5-Amino-4-imidazolecarboxamide riboside
  7-Methyl-5-propyl-s-triazole[1,5c]pyrimidine-2-amine
  7-(2-Hydroxyethoxy)-9-oxoxanthene-2-carboxylic acid
  Amiloride
  Cloxacepride
  Deoxycoformycin
  Fisetin
  Flufenamic acid
  Nilidrine hydrochloride
  p-Bromophenacyl bromide
  Pimozide Phosphatase inhibitors make up another class of compounds which is characterized by mast cell degranulation-inhibitory activity. Exemplary compounds in this class are Nedocromil, Minocromil, Kaempferol, Quercetin, 2'-carboxyl-atochromone-5'-yl-2-hydroxypropane derivatives, 1,3-bis [2'-[[(acetoxymethyl)oxyl]carbonyl] chromone-5'-yl]2-hydroxypropane, pyrano [3,2,-g] quinoline-2,8-dicarboxylic acid derivatives, and 5-chlorobenzoxazole-2-carboxylic acid. These compounds and others in this class obstruct a phoshatase from mediating protein dephosphorylation, an integral step in various phosphorylation/dephosphorylation events which are essential to intracellular regulation.

In particular, protein phosphatase inhibitors have been shown to attenuate the release of histamine and leukotriene mediators from human lung mast cells. Peachell et al., *J. Immunol.* 151: 3808 (1993). Phosphatase inhibitors are distinguishable by an ability to inhibit one of the four major classes of phosphatases. Type 1 phosphatase (PP1) dephosphorylates the beta subunit of phosphorylase kinase and is inhibited by thermostable inhibitors 1 and 2 and inactivated by okadaic acid (LC Services Corporation, Nottingham, UK). Type 2 phosphatases include three subtypes (PP2A, PP2B, and PP2C), each of which dephosphorylates the alpha subunit of phosphorylase kinase. Each of PP2A and PP2B are inhibited by okadaic acid. PP2C is insensitive to okadaic acid but is completely dependent on $Mg^{2+}$.

Accordingly, the class of protein phosphatase inhibitors also includes okadaic acid, analogues of okadaic acid, okadaol and nor-okadaone (LC Services Corporation, supra; Biomol, Plymouth Meeting, Pa.), and okadaic acid methyl ester [see Nishiwaki, *Carcinogenesis* 11: 1837 (1990)], as well as calyculin (LC Services Corporation).

It is not necessary to the operability of the present invention that each member of the foregoing classes inhibits mast cell degranulation to the same extent. The ability of a particular substance to inhibit mast cell degranulation can be readily determined empirically. Thus, mast cells from rats (pieces of small intestine) or humans (intestinal biopsies) can be obtained; otherwise, RBL cells or immortalized human mucosal-like mast cells (HMC-1) are kept in culture. Any of these cells then are exposed to various concentrations of a putative inhibitory compound, to allow for action by the putative inhibitor at critical sites. Efficacy with respect to inhibition of mast cell degranulation then is ascertained; that is, the intestinal biopsies, explants or cultured cells thus treated are used as such or washed free of unbound test compound before exposure to a stimulus known to induce mast cell degranulation. A compound suitable for use in accordance with the present invention is recognized as one that prevents the stimulus from causing degranulation, presumably by binding to specific receptors or by inactivating a crucial step in the degranulation process.

While it is possible in principle that a particular compound in one of the above-mentioned classes, by virtue of its activity, could be employed in the described manner, it is true generally that the advisability of using any mast cell-degranulation inhibitor according to the present invention must be tempered by clinical considerations, including toxicity, bioavailability, distribution, half-life and clearance, which are conventional to this field. See, for example, GOODMAN AND GILMAN'S THE PHARMACOLOGICAL BASIS OF THERAPEUTICS § I & XVII (7th ed.).

Thus, dosage forms for the delivery of the selected mast cell degranulation blocking agent should be those that achieve and retain high levels of the drug in the gastrointestinal tract with reasonable rapidity. These dosage forms are adapted for a variety of conventional routes of administration, including oral, parenteral and rectal.

Pursuant to the present invention, a mast cell degranulation-blocking agent is administered in a pharmaceutically effective amount. The dosage range for pharmaceutical effectiveness can be determined by reference to standard laboratory tests for inhibition of gastrointestinal mast cell degranulation, as discussed above.

A pharmaceutically effective dose for a given mast cell degranulation-blocking agent can be approximated by its $ID_{20}$, which is the dose necessary to cause 20% inhibition in mast cells when applied to mast cells stimulated in vitro. The $ID_{20}$ values for selected inhibitor compounds are shown in Table 2.

TABLE 2

COMPOUNDS WHICH INHIBIT RAT MUCOSAL MAST CELL DEGRANULATION IN VITRO

| Compound | $ID_{20}$ for histamine release |
|---|---|
| Azatadine | $10^{-7}$ M |
| Hydroxyzine | $5 \times 10^{-5}$ M |
| Ketotifen | $10^{-5}$ M |
| $N^\alpha$-methyl histamine | $10^{-7}$ M |
| Oxatomide | $10^{-7}$ M |
| Spermine | $5 \times 10^{-5}$ M |
| Tamoxifen | $5 \times 10^{-5}$ M |

$ID_{20}$ = inhibitory dose causing 20% inhibition.
M = molar concentration.

The agent can best be administered systemically or directly in the intestinal loops (suppository, enema or injection) of the live mammal. The mast cell inhibitory effect of certain of these compounds has been described for non-intestinal mast cells. See, for example, Vliagoftis et al., *Biochem. Pharmacol.* 43: 2237–45 (1992), Rozniecki et al. in PROC. 8TH INT'L CONGRESS IMMUNOLOGY 159 (Budapest 1992), Rozniecki et al., FASEB J. 6: A1554 (1992), and Rachmilewitz et al., Gastroenterol. 102:A235 (1992).

An assay by which efficacy of a mast cell degranulation-blocking agent can be tested systemically in the present context is the rat-immobilization assay, in which a rat is pre-treated with an agent and then restrained for one hour in a clear plexiglass cylinder. After the immobilization, a specific gastrointestinal mast cell mediator, rat mast cell protease II (RMCPII), is measured. This assay is accepted as a non-ulcerogenic model of stress. See Williams et al., *Am. J. Physiol.* 253:582–86 (1987).

Results from testing ketotifen in the rat-immobilization assay are presented in Table 3 below. Ketotifen was administered intraperitoneally to rats (1 mg/kg body weight, twice daily) for four days prior to immobilization.

TABLE 3

INHIBITION BY KETOTIFEN OF
RAT INTESTINAL RMCPII IN A STRESS MODEL

| Time (min) | Immobilized (n = 3) | Non-immobilized (n = 3) | Pre-treated w/ ketotifen (n = 3) |
|---|---|---|---|
| 60 | 4.85@ | 0.3 | 0.5 |
| 120 | 12.4* | 0.7 | 0.8** |

@ng/ml; n = number of rats tested
*$p < 0.05$ vs. non-immobilized
**$p < 0.001$ vs. immobilized Table 3 shows that intestinal mast cells are activated during stress to secrete a specific proteolytic enzyme, RMCPII, and that ketotifen acts as a mast cell degranulation-blocking agent in preventing secretion of RMCPII from such cells. The equivalent proteolytic enzyme in humans is tryptase, which also can be measured from colonic fluid or biopsies.

It is essential to the present invention that the selected agent inhibit mucosal mast-cell secretion. Thus, mast cell degranulation-blocking agents, such as disodium cromoglycate (CROMOLYN), which do not have an inhibitory effect specifically on mucosal mast cells, see Pearce et al., *J. Immunol.* 128:2481–86 (1982), are not within the scope of the present invention. No work has so far involved H3 receptor agonists in the inhibition of gastrointestinal mast cell degranulation.

A mast cell degranulation-blocking agent can be administered, according to the present invention, in the form of the active agent itself or as a pharmaceutically acceptable salt of the active agent. The phrase "pharmaceutically acceptable salt" denotes a non-toxic, substantially non-irritating salt of the compound used. Typical salts are ammonium salts and salts containing an cation that is an alkali metal or alkaline earth metal, such as sodium, potassium, calcium or magnesium. The category of suitable cations for the salt also includes sulphate, phosphate, tartrate and citrate. Other acceptable salts are those with non-toxic organic acids, such as fatty acids of one to six carbon atoms in length.

Pursuant to the present invention, a mast cell degranulation-blocking agent can be delivered via methods known for drug administration. The agents are typically administered as pharmaceutical compositions in combination with pharmaceutically acceptable carriers. Such compositions may be prepared from conventional materials by procedures well known in the art.

Compositions within the present invention can be adapted for oral or parenteral administration, as well as for enteral administration or through mucous membranes, such as transdermally. An oral formulation which will keep the drug for an extended time in the gastrointestinal tract is preferred, since such a formulation allows long exposure of the mucosal mast cells present there to the drug.

Forms suitable for oral administration include tablets, dispersible powders, granules, capsules, syrups, elixirs and suspensions. Also preferred in this regard are encapsulated forms. For instance, a preferred mode of administration would be via liposomes, multilammelar phospholipid vesicles, or lipospheres, which protect the active agent from destruction in the stomach and allows for slow release in the intestine as each phospholipid layer is dissolved, resulting in sustained high intestinal levels of the drug. Alving, C. R., S. Shichijo, I. Mattsby-Baltzec, R. L. Richards and N. M. Wassef, "Preparation and Use of Liposomes in Immunologic Studies," in LIPOSOME TECHNOLOGY, 2nd ed., vol. III, G. Gregoriadis, ed., CRC Press, Boca Raton, FL, pp.317–343, 1984; Amselem, S., C. R. Alving, and A. J. Domb, *Polymers for Advanced Technologies*, 3:351–357 (1992); and Amselem, et al. Vaccine Research 1: 383–385 (1992).

Compositions for oral use contain one or more conventional adjuvants, such as sweetening agents, flavoring agents, coloring agents and preserving agents, in order to provide a presentable and palatable preparation. Tablets may contain the active ingredients in a mixture with conventional pharmaceutically acceptable excipients. These include inert carriers, such as calcium carbonate, sodium carbonate, lactose, and talc; granulating and disintegrating agents, such as starch and alginic acid; binding agents such as starch, gelatin acacia; and lubricating agents, such as magnesium stearate, stearic acid and talc. Tablets may be uncoated or coated by known techniques to delay disintegration and absorption in the gastrointestinal tract, thereby providing a sustained action over a longer period of time. Similarly, suspensions, syrups and elixirs may contain active ingredients in mixture with any of the conventional excipients utilized in the preparation of such compositions. This includes suspending agents such as methylcellulose, tragacanth and sodium alginate; wetting agents such as lecithin, polyoxyethylene stearate or polyoxyethylene sorbitan monoleate; and preservatives. Capsules may contain the active ingredients alone or in an admixture with an inert solid carrier, such as calcium carbonate, calcium phosphate or kaolin. These pharmaceutical compositions may contain up to 90% of active ingredients in combination with the carrier or adjuvant. The compounds preferably are put up in unit dosage forms, particularly for oral administration, for example, in 20 mg tablets. Such forms may contain the active ingredient separately, for example in separate layers.

The agents can be administered in sustained release form or in divided dosages.

Oral administration often is preferred if the mast cell degranulation-blocking agent is orally active. Transdermal administration also is preferred. More specifically, in the case of mast cell degranulation-blocking agents which are substantially destroyed or deactivated upon oral administration, or where a more prolonged duration of activity is desired, a mast cell degranulation-blocking agent also can be administered transdermally or via other body membranes, such as rectally.

A preferred formulation within the present invention comprises both a suitable mast cell-degranulation inhibitor and an agent that inhibits or counteracts intestinal motility, thereby increasing the transit time and, hence, the effect of the inhibitor in the intestinal tract. Such a suitable antimotility agent is dicyclomine capsules, such as BENTYL (Taylor Pharmaceutical Company, Decatur, Ill.). The use of an antimotility agent in this context is especially preferred when the mast cell-degranulation inhibitor is contained in a lipid-containing delivery vehicle, as discussed above. Thus, the antimotility agent can be "co-administered" with the delivery vehicle, i.e., can be administered in such a way that the motility-counteractive influence of the agent increases the residence time of the delivery vehicle in the intestine.

The following illustrative examples further describe the present invention.

EXAMPLE 1

The following experiment was performed in order to evaluate rat mucosal mast cell (MMC) degranulation by measuring rat mast cell protease II (RMCPII), a specific marker for MMC, and by electron microscopy.

Rats were treated intragastrically for four (4) days with either 0.5 ml of saline containing ketotifen (1 mg/kg twice daily) or saline alone. On day five, the animals were euthanized, ileum was removed and ileal explants were placed in organ culture. The explants were incubated at 37° C. in a medium containing either 5 µg/ml of toxin A in 0.01 ml of 50 mM Tris buffer, or buffer alone. Aliquots (50 µl) of medium were collected at specified times and RMCPII levels were determined. Results are expressed in Table 4 as nanograms of RMCPII released per milligram of tissue wet weight (Pothoulakis et al., *Gastroenterology* 105:701–707, 1993).

TABLE 4

INHIBITION BY KETOTIFEN OF RAT INTESTINAL RMCP II SECRETION INDUCED BY TOXIN A

| Time (min) | Buffer (n = 10) | Toxin A (n = 7) | Ketotifen+ Toxin A (n = 6) |
|---|---|---|---|
| 30 | 3.4 ± 0.8 | 5.0 ± 1.2 | 2.9 ± 1.0 |
| 60 | 6.2 ± 0.9 | 7.2 ± 1.7 | 3.0 ± 1.1+ |
| 120 | 7.6 ± 1.2 | 12.6 ± 2.1* | 4.2 ± 0.9++ |
| 180 | 11.3 ± 2.1 | 24.0 ± 4.8** | 6.7 ± 1.9++ |

*$p < 0.05$ vs buffer
**$p < 0.01$ vs buffer
+$p < 0.05$ vs Toxin A
++$p < 0.01$ vs Toxin A Electron microscopy showed significant mucosal mast cell degranulation in rat ileum within 15 minutes of exposure to toxin A, and complete degranulation at 60 minutes. These results, obtained by J. Castagliuolo, J. T. LaMont, R. Letourneau, C. Kelly, J. C. O'Keane, A. Jaffer, T. C. Theoharides and C. Pothoulakis, demonstrate that ketotifen effectively inhibits the release of RMCPII from rat ileal explants and, hence, inhibits mucosal mast cell degranulation.

Similar results were obtained using the substance P receptor antagonist (Pothoulakis et al., *Proc. Natl. Acad. Sci., USA* 91:947–951, 1994).

EXAMPLE 2

A female patient, age 49, suffered from irritable bowel syndrome for approximately 10 years. Symptoms were so severe that she had difficulty in functioning as a nurse, mother and wife. After treatment with hydroxyzine hydrochloride (ATARAX; 50 mg/day) for three months, her gastrointestinal discomfort was almost completely eliminated, and she was able to resume her professional and family responsibilities. On several occasions when she attempted to withdraw from the use of hydroxyzine hydrochloride, she experienced a marked increase in symptoms of irritable bowel syndrome. The symptoms disappeared when she resumed taking the medication.

EXAMPLE 3

A female patient, age 32, had a four-year history of irritable bowel syndrome and had difficulty in carrying out her professional duties as a nurse. She was treated for 4 months with 50 mg/day of hydroxyzine pamoate (VISTARIL). She experienced a noticeable improvement of her symptoms and was able to resume her professional activities.

EXAMPLE 4

A female patient, age 39, suffered from irritable bowel syndrome for over two years. Her symptoms included constant pain at the connection of the buttocks with the upper legs, as well as painful defecation. After treatment with ketotifen (ZADITEN; 4 mg/day) for two months, her pain subsided significantly.

EXAMPLE 5

A female patient, age 39, with a five-year history of irritable bowel syndrome, experienced constant abdominal pain which was not relieved by any of a variety of narcotic and non-narcotic analgesics and anti-inflammatory drugs. Her symptoms were exacerbated during menstruation. Treatment with tamoxifen citrate (NOVADEX; 40 mg/day, administered orally) for two months substantially eliminated her pain.

EXAMPLE 6

A female patient, age 32, with a two-year history of abdominal migraine, experienced constant gastrointestinal pain which was considerably worse immediately premenstrually. After treatment with the Gn-RH analogue LUPRON (3 µg/day subcutaneous injection) for four months, she was symptom-free.

What is claimed is:

1. A method of treatment of a patient suffering from an endogenous, painful gastrointestinal condition of non-inflammatory, non-ulcerative origin comprising the step of administering to said patient an effective amount of a mast cell degranulation-blocking agent.

2. A method according to claim 1, wherein said mast cell degranulation-blocking agent is a naturally occurring polyamine.

3. A method according to claim 1, wherein said mast cell degranulation-blocking agent is selected from the group consisting of spermine, spermidine, and metabolites thereof.

4. A method as claimed in claim 3, wherein said mast cell degranulation-blocking agent is spermine.

5. A method as claimed in claim 1, wherein said mast cell degranulation-blocking agent is administered orally.

6. A method as claimed in claim 1, wherein said mast cell degranulation-blocking agent is contained in a lipid-containing delivery vehicle.

7. A method as claimed in claim 6, wherein said lipid-containing delivery vehicle is co-administered with an antimotility agent.

8. A method as claimed in claim 1, wherein said mast cell degranulation-blocking agent is a heterocyclic histamine-1 receptor antagonist.

9. A method as claimed in claim 1, wherein said mast cell degranulation-blocking agent is selected from the group consisting of azatadine, azelastine, cetirizine, forskolin, hydroxyzine, ketotifen and oxatomide.

10. A method as claimed in claim 9, wherein said mast cell degranulation-blocking agent is ketotifen.

11. A method as claimed in claim 10, wherein said ketotifen is in the form of a pharmaceutically acceptable salt.

12. A method as claimed in claim 1, wherein said mast cell degranulation-blocking agent is a histamine-3 receptor agonist.

13. A method as claimed in claim 1, wherein said last cell degranulation-blocking agent is selected from the group consisting of $N^\alpha$-dimethyl histamine, $R^\alpha$-methyl histamine, $\alpha,\beta$-dimethyl-$N^\alpha$(dimethyl) histamine, $\alpha,\beta$-difluoro-$N^\alpha$(dimethyl) histamine, $\alpha$-methyl,$\beta$-fluoro-$N^\alpha$(fluoromethyl) histamine and $\alpha,\beta$-difluoro-$N^\alpha$(fluoromethyl) histamine.

14. A method as claimed in claim 13, wherein said mast cell degranulation-blocking agent is $\alpha,\beta$-difluoro-$N^\alpha$(fluoromethyl) histamine.

15. A method as claimed in claim 1, wherein said mast cell degranulation-blocking agent is an anti-female sex hormone.

16. A method as claimed in claim 1, wherein said mast cell degranulation-blocking agent is clomiphene, mifepristone, tamoxifen and a GnRH analogue.

17. A method as claimed in claim 16, wherein said mast cell degranulation-blocking agent is tamoxifen.

18. A method as claimed in claim 16, wherein said mast cell degranulation-blocking agent is leuprolide acetate.

19. A method as claimed in claim 18, wherein said leuprolide acetate is administered subcutaneously.

20. A method as claimed in claim 1, wherein said condition is abdominal migraine.

21. A method as claimed in claim 1, wherein said condition is irritable bowel syndrome.

\* \* \* \* \*